(12) United States Patent
Murakami et al.

(10) Patent No.: US 7,368,268 B2
(45) Date of Patent: May 6, 2008

(54) CORYNEFORM BACTERIUM TRANSFORMANT AND PROCESS FOR PRODUCING DICARBOXYLIC ACIDS USING THE SAME

(75) Inventors: Shikiko Murakami, Soraku-gun (JP); Kaori Nakata, Soraku-gun (JP); Shohei Okino, Soraku-gun (JP); Yuko Ikenaga, Soraku-gun (JP); Masayuki Inui, Soraku-gun (JP); Hideaki Yukawa, Soraku-gun (JP)

(73) Assignee: Research Institute of Innovative Technology for the Earth, Kyoto (JP)

( * ) Notice: Subject to any disclaimer, the term of this patent is extended or adjusted under 35 U.S.C. 154(b) by 0 days.

(21) Appl. No.: 10/566,129

(22) PCT Filed: Jul. 28, 2004

(86) PCT No.: PCT/JP2004/010706

§ 371 (c)(1),
(2), (4) Date: Mar. 2, 2006

(87) PCT Pub. No.: WO2005/010182

PCT Pub. Date: Feb. 3, 2005

(65) Prior Publication Data

US 2007/0087423 A1    Apr. 19, 2007

(30) Foreign Application Priority Data

Jul. 29, 2003   (JP)   ............................ 2003-281933

(51) Int. Cl.
*C12P 7/46*   (2006.01)
*C12N 1/21*   (2006.01)
*C07H 21/04*  (2006.01)

(52) U.S. Cl. .................. 435/145; 435/252.3; 435/69.1; 435/252.32; 536/23.2

(58) Field of Classification Search ...................... None
See application file for complete search history.

(56) References Cited

U.S. PATENT DOCUMENTS 6,852,516 B2 *   2/2005   Hibino et al. ............... 435/110

FOREIGN PATENT DOCUMENTS

| JP | 11-196888 | 7/1999 |
| JP | 11-206385 | 8/1999 |
| WO | 99/53035 | 10/1999 |

OTHER PUBLICATIONS

Murakami et al., "Development of a New Bioprocess Invovling Cornye-form Bacteria-Analysis of the Pathway of Anaerobic Metabolism using High Gene Expression Strains", The Meeting Summaries and Lecture Abstracts of the 2003 Annual Meeting of JSBBA (The Japan Society for Bioscience, Biotechnology, and Agrochemistry) held in Tokyo, Japan, Abstract 2A11p07, published Mar. 5, 2003. (with English translation).

G. N. Vemuri et al., "Effects of Growth Mode and Pyruvate Carboxylase on Succinic Acid Production by Metabolically Engineered Strains of *Escherichia coli*", Applied and Environmental Microbiology, vol. 68, No. 4, pp. 1715-1727, Apr. 2002.

R. R. Gokarn et al., "The Physiological Effects and Metabolic Alterations Caused by the Expression of *Rhizobium etli* Pyruvate Carboxylase in *Escherichia coli*", Applied Microbiology Biotechnology, vol. 56, No. 1-2, pp. 188-195, Jul. 2001.

A. M. Sanchez et al., "Efficient Succinic Acid Produciton from Glucose through Overexpression of Pyruvate Carboxylase in an *Escherichia coli* Alcohol Dehydrogenase and Lactate dehydrogenase Mutant", Biotechnol. Prog., vol. 21, pp. 358-365, Mar. 2005.

* cited by examiner

*Primary Examiner*—Ponnathapu Achutamurthy
*Assistant Examiner*—Md Younus Meah
(74) *Attorney, Agent, or Firm*—Wenderoth, Lind and Ponack, L.L.P.

(57) ABSTRACT

The present invention provides an aerobic coryneform bacterium transformant in which a lactate dehydrogenase gene is disrupted, and a pyruvate carboxylase gene is recombined so as to be highly expressed by a genetic engineering method. The aerobic coryneform bacterium transformant of the present invention can produce dicarboxylic acids from saccharides at a high production rate.

2 Claims, No Drawings

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial Sequence
```

```
<220> FEATURE:
<223> OTHER INFORMATION: Primer

<400> SEQUENCE: 1
ctctgtcgac atcaggaagt gggatcgaaa                              30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
ctctgtcgac ttccatccaa cagtttcatt                              30

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ctctgttaac acaacaagac ccatcatagt                              30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
ctctgttaac acatgcagtc atgtcgtgct                              30

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
ctctgatatc gttccactga gcgtcagacc                              30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
ctctgatatc tccgtcgaac ggaagatcac                              30

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
ctctacatgt tgcaggtcag aggagtgt                                28
```

```
<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
ctctgcatgc aggaatcgtg tgcatggtc                                    29

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ctctgtcgac agcacagcct taaagca                                      27

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
ctctgtcgac ttgtgcagca agacgaaa                                     28

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
ctctgcatgc ggatgccgtt tcgctcatag                                   30

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ctctgcatgc taataaggcg cagagcgtcg                                   30
```

CORYNEFORM BACTERIUM TRANSFORMANT AND PROCESS FOR PRODUCING DICARBOXYLIC ACIDS USING THE SAME

This application is a U.S. national stage of International Application No. PCT/JP2004/010706 filed Jul. 28, 2004.

TECHNICAL FIELD

Dicarboxylic acids are used in a wide variety of applications such as raw materials for polymer synthesis or for medicaments, and cosmetic use or food additive use. For example, succinic acid and its derivatives are expected to be further expanded in its demand for use in biodegradable plastic raw materials or green cleaning solvents with no environmental pollution.

The present invention relates to a coryneform bacterial transformant and a process for producing a dicarboxylic acid using the same. More particularly, the present invention relates to a highly productive process for producing dicarboxylic acids using a coryneform bacterium which has been subjected to specific transformation treatment.

BACKGROUND ART

Previously, in order to produce an objective substance at a high production rate by a bio procedure, many attempts have been tried to enhance expression of a catalyst enzyme gene involved in any one of metabolic pathways of microorganisms to an objective substance. It is identified that a dicarboxylic acid intervening in the tricarboxylic acid cycle such as succinic acid and the like is produced by incorporating carbonate ion from phosphoenolpyruvic acid or pyruvic acid produced in a glycolytic pathway of saccharides through a catalytic action of phosphoenolpyruvate carboxylase (hereinafter, referred to as PEPC) or pyruvate carboxylase (hereinafter, referred to as PC), wherein a reductive tricarboxylic acid cycle reaction via oxaloacetic acid takes place.

Based on above mentioned metabolic pathways, as a process for producing organic acid such as malic acid, fumaric acid, succinic acid and the like using a coryneform bacterium, a method of recombining a PEPC gene (Japanese Patent Application Laid-Open No. 11-196887) and a method of recombining a PC gene (Japanese Patent Application Laid-Open No. 11-196888) have been proposed.

However, the production rate of organic acid such as succinic acid and the like by any of these methods is not sufficient, and further improvement is needed.

On the other hand, there has been proposed a technique of simultaneously producing succinic acid, acetic acid and ethanol using an *Escherichia coli* mutant deficient in a lactate dehydrogenase (hereinafter, referred to as ldh) gene (enzyme gene involved in production route of lactic acid from pyruvic acid) which is one of the essential features of the present invention (U.S. Pat. No. 5,770,435, U.S. Pat. No. 5,869,301). The *Escherichia coli* mutant used in these US patents is an *Escherichia coli* mutant (AFP 111 strain) obtained by transforming an *Escherichia coli* strain (NZN 111 strain) deficient in an ldh gene and a pfl gene (pyruvate formate-lyase gene) so as to be capable of producing simultaneously succinic acid, acetic acid and ethanol, by mutation treatment (a mutated expression gene is not expressly described) or recombination treatment (treatment by introduction of a plasmid containing malate dehydrogenase-mdh-gene) under the anaerobic condition.

These two US patents have the similar technical contents by the same inventors. Although the present invention and these two US patents use respectively different organism species, but, similarly deficient in ldh gene expression function which is an essential feature of the present invention, the contents of metabolism function of a microorganism to be transformed are entirely different in view of the technical contents and results based on respective inventive concepts.

The difference in metabolism function between a coryneform bacterium transformant used in the present invention and the aforementioned *Escherichia coli* mutant is clear from the following two facts.

1) The *Escherichia coli* mutant (AFP 111) is further transformed by mutation or recombination of the *Escherichia coli* strain (NZN 111 strain) which is impossible in anaerobic growth because of deficiency in both genes of an ldh gene and a pfl gene, so as to have ethanol production function.

But a recombinant coryneform bacterium used in the present invention has not ethanol production function at all.

2) The *Escherichia coli* mutant (AFP 111) has not an essential requirement for the supply of carbonate ion in the production of succinic acid from saccharides (related with the above 1, since AFP 111 has an ethanol- and acetic acid-producing function, it is presumed that carbon dioxide gas produced as a byproduct of these fermentation products is utilized). In the production of dicarboxylic acids such as succinic acid and the like from saccharides by a coryneform bacterium of the present invention, it is essential to supply carbonate or bicarbonate ions or carbon dioxide gas from the outside.

Like this, it is thought that the *Escherichia coli* mutant and a coryneform bacterium of the present invention which are similarly deficient in an ldh gene have the entirely different metabolism functions and mechanisms. It is clear that the technique of the present invention is not obtained by combining two US patents regarding an *Escherichia coli* mutant (AFP 111) (in the present invention, mutation treatment and recombination technique of these US patents are not used) and the technique of the two Japanese Laid-Open Publications regarding a coryneform bacterium, and technical constitutional contents thereof are different.

Regarding production of succinic acid, the ldh gene-disrupted effect is made clear in Japanese Patent Application National Publication (Laid-Open) No. 2002-511250. In this published patent application, succinic acid production behavior is investigated regarding each of an ldh gene-disrupted mutant of an *Escherichia coli* wild strain (MG1655) and a double recombinant of PC gene high expression (although *Escherichia coli* wild strain has not originally a PC gene, introduction of a foreign PC gene is also called "high expression")/ldh gene disruption (see Japanese Patent Application National Publication (Laid-Open) No. 2002-511250, Example II, Table 4).

In the same Table, it is shown that disruption of an ldh gene of an *Escherichia coli* wild strain hardly influences on succinic acid production (has little effect), and disruption of an ldh gene exhibits an inhibitory effect on the potentiation of succinic acid production by high expression of a PC gene.

These results show that although disruption, inhibition or interruption of a pathway other than a pathway of metabolism from pyruvic acid to succinic acid (e.g. pathway of production of lactic acid from pyruvic acid) in order to potentiate the flow of a carbon substance in the metabolic pathway from pyruvic acid to an objective substance (succinic acid) could be expected to have an effect of accumulating pyruvic acid flowing to an objective substance (effect of increasing amount of substrate), and such transformations are thought as if they are an easily thinkable means, the fact is converse. That is, it is shown that disruption of an ldh gene cannot be said to primarily lead to positive effect to succinic acid production.

DISCLOSURE OF THE INVENTION

The present invention provides a technique of producing dicarboxylic acids intervening in the tricarboxylic acid cycle such as succinic acid and the like at a high production rate, using an aerobic coryneform bacterial transformant by a novel process which has previously been not known. That is, an object of the present invention is to provide a technique by which an aerobic coryneform bacterium which has been subjected to particular transformation treatment is produced, and dicarboxylic acids can be produced at high rate with high reaction selectivity from saccharides under the particular reaction conditions.

In order to produce dicarboxylic acids intervening the tricarboxylic acid cycle such as succinic acid and the like from saccharides at high production rate using an aerobic coryneform bacterium, the present inventors variously studied using a PEPC high expression transformant coryneform bacterium and a PC high expression transformant coryneform bacterium, but the dicarboxylic acids could not be produced at a desired high production rate. By such the process, the production rate was only the approximately same as a production rate when a coryneform bacterium before transformation was used.

However, unexpectedly, when a PC high expression transformant was produced using an ldh gene-disrupted coryneform bacterium strain involved in lactic acid fermentation pathway different from the tricarboxylic acid cycle ("disruption" of an ldh gene in the present invention means that all or a part of an ldh gene is disrupted, or mutated, or has not ldh expression activity by alteration or deletion of a gene expression unit such as a promoter, a ribosome binding site and the like of the gene), and saccharides was reacted therewith under the particular reducing state in the present invention, it was found that a dicarboxylic acid is produced at a high production rate which is 2-fold compared to that of the dicarboxylic acid production by a simple PC high expression transformant in which an ldh gene is not disrupted. The present inventors further studied to arrive at the present invention (in the case of PEPC high expression transformant, such effect was not recognized as is revealed in Comparative Example described later).

That is, the present invention relates to:

(1) an aerobic coryneform bacterial transformant, wherein a lactate dehydrogenase gene is disrupted and a pyruvate carboxylase gene is recombined so as to be highly expressed, and wherein said aerobic coryneform bacterium is one selected from the group consisting of *Corynebacterium*, *Brevibacterium*, *Arthrobacter*, *Mycobacterium* and *Micrococcus*, (2) the aerobic coryneform bacterial transformant according to the above (1), wherein the *Corynebacterium* is any one of bacteria selected from *Corynebacterium glutamicum* R, *Corynebacterium glutamicum* ATCC 13032, *Corynebacterium glutamicum* ATCC 13058, *Corynebacterium glutamicum* ATCC 13059, *Corynebacterium glutamicum* ATCC 13060, *Corynebacterium glutamicum* ATCC 13232, *Corynebacterium glutamicum* ATCC 13286, *Corynebacterium glutamicum* ATCC 13287, *Corynebacterium glutamicum* ATCC 13655, *Corynebacterium glutamicum* ATCC 13745, *Corynebacterium glutamicum* ATCC 13746, *Corynebacterium glutamicum* ATCC 13761, *Corynebacterium glutamicum* ATCC 14020 and *Corynebacterium glutamicum* ATCC 31831, (3) the aerobic coryneform bacterial transformant according to the above (1), wherein the *Brevibacterium* is any one of bacteria selected from *Brevibacterium lactofermentum* ATCC 13869, *Brevibacterium flavum* MJ-233, *Brevibacterium flavum* MJ-233AB-41 and *Brevibacterium ammoniagenes* ATCC 6872, (4) the aerobic coryneform bacterial transformant according to the above (1), wherein the *Arthrobacter* is any one of bacteria selected from *Arthrobacter globiformis* ATCC 8010, *Arthrobacter globiformis* ATCC 4336, *Arthrobacter globiformis* ATCC 21056, *Arthrobacter globiformis* ATCC 31250, *Arthrobacter globiformis* ATCC 31738 and *Arthrobacter globiformis* ATCC 35698, (5) the aerobic coryneform bacterial transformant according to the above (1), wherein the *Mycobacterium* is *Mycobacterium bovis* ATCC 19210 or *Mycobacterium bovis* ATCC 27289, (6) the aerobic coryneform bacterial transformant according to the above (1), wherein the *Micrococcus* is any one of bacteria selected from *Micrococcus freudenreichii* No. 239, *Micrococcus luteus* No. 240, *Micrococcus ureae* IAM 1010 and *Micrococcus roseus* IFO 3764, (7) the aerobic coryneform bacterial transformant according to the above (2), wherein the *Corynebacterium* is *Corynebacterium glutamicum* R (8) the aerobic coryneform bacterial transformant according to any one of the above (1) to (7), wherein a lactate dehydrogenase gene is disrupted in such a manner that said gene is interrupted, or a part or the whole region of the gene is deleted by a method selected from a homologous recombination method, a transposon insertion method and a mutagen introduction method, and an expression function for the lactate dehydrogenase activity is lost, (9) the aerobic coryneform bacterial transformant according to any one of the above (1), (2), (7) and (8), which is *Corynebacterium glutamicum* R ldh$^-$/pCRB1-PC or *Corynebacterium glutamicum* R ldh$^-$/pCRB1-PC-FRD,

(10) a process for producing dicarboxylic acids, which comprises reacting a bacterium and saccharides in a reaction solution under the reducing state containing carbonate or bicarbonate ions or carbon dioxide gas, and collecting dicarboxylic acids produced in the reaction solution, wherein the bacterium is the aerobic coryneform bacterial transformant as defined in the above (1),

(11) the process for producing dicarboxylic acids according to the above (10), wherein an oxidation-reduction potential of the reaction solution under the reducing state is −200 millivolts to −500 millivolts, and

(12) the process for producing dicarboxylic acids according to the above (10) or (11), wherein the dicarboxylic acids is selected from succinic acid, fumaric acid and malic acid.

EFFECTS OF THE INVENTION

According to the present invention, dicarboxylic acids can be produced from saccharides at high production rate. In the present invention, there is used an aerobic coryneform bacterium transformant in which a lactate dehydrogenase gene is disrupted and a pyruvate carboxylase gene is recombined so as to be highly expressed by the genetic engineering procedure. This transformant produces a dicarboxylic acid at a high production rate which is 2-fold, as compared with use of a simple PC high expression transformant in which an ldh gene is not disrupted.

BEST MODE FOR CARRYING OUT THE INVENTION

An aerobic coryneform bacterium used in the present invention is a group of microorganisms defined in Bargeys Manual of Determinative Bacteriology, 8, 599, 1974. Examples of the bacteria include *Corynebacterium, Brevibacterium, Arthrobacter, Mycobacterium*, and *Micrococcus*.

Further specifically, examples of the *Corynebacterium* include *Corynebacterium glutamicum* R (FERM P-18976), *Corynebacterium glutamicum* ATCC 13032, *Corynebacterium glutamicum* ATCC 13058, *Corynebacterium glutamicum* ATCC 13059, *Corynebacterium glutamicum* ATCC 13060, *Corynebacterium glutamicum* ATCC 13232, *Corynebacterium glutamicum* ATCC 13286, *Corynebacterium glutamicum* ATCC 13287, *Corynebacterium glutamicum* ATCC 13655, *Corynebacterium glutamicum* ATCC 13745, *Corynebacterium glutamicum* ATCC 13746, *Corynebacterium glutamicum* ATCC 13761, *Corynebacterium glutamicum* ATCC 14020 and *Corynebacterium glutamicum* ATCC 31831.

Examples of the *Brevibacterium* include *Brevibacterium lactofermentum* (ATCC 13869), *Brevibacterium flavum* MJ-233 (FERM BP-1497) or *Brevibacterium flavum* MJ-233AB-41 (FERM BP-1498), and *Brevibacterium ammoniagenes* (ATCC 6872).

Examples of the *Arthrobacter* include *Arthrobacter globiformis* ATCC 8010, *Arthrobacter globiformis* ATCC 4336, *Arthrobacter globiformis* ATCC 21056, *Arthrobacter globiformis* ATCC 31250, *Arthrobacter globiformis* ATCC 31738 and *Arthrobacter globiformis* ATCC 35698.

Examples of the *Mycobacterium* include *Mycobacterium bovis* ATCC 19210 and *Mycobacterium bovis* ATCC 27289.

Examples of the *Micrococcus* include *Micrococcus freudenreichii* No. 239 (FERM P-13221), *Micrococcus luteus* No. 240 (FERM P-13222), *Micrococcus ureae* IAM 1010 and *Micrococcus roseus* IFO 3764.

As the aerobic coryneform bacterium used in the present invention, the *Corynebacterium glutamicum* R (FERM P-18976), *Corynebacterium glutamicum* ATCC 13032 and *Brevibacterium lactofermentum* ATCC 13869 are preferable.

In addition, the aerobic coryneform bacterium used in the present invention may be a mutant of a wild strain present in the nature (e.g. a mutant of *Corynebacterium glutamicum* R strain which has acquired assimilation ability of cellobiose, FERM P-18977, FERM P-18978 strain; see Japanese Patent Application Laid-Open No. 2004-89029), or an artificial strain in which a gene other than a constitutional gene of the present invention is recombined (e.g. an artificial strain of *Corynebacterium glutamicum* R strain which has been transformed so as to express a simultaneous assimilation ability of glucose and cellobiose, by genetic recombination regarding a phosphotransferase enzyme II, FERM P-18979; see Japanese Patent Application Laid-Open No. 2004-89029).

These above mentioned aerobic coryneform bacteria are subjected to disruption of ldh gene expression and transformation treatment of PC high expression described in detail later, for the purpose of the object of the invention.

Disruption of an ldh gene of the present invention is such that the gene is interrupted, or a part or the whole region of the gene is removed by a method selected from a homologous recombination method, a transposon insertion method and a mutagen introduction method, and the enzyme activity expressing function can be lost, but since a transposon insertion method and a mutagen introduction method are to randomly disrupt a gene on a chromosome and, in order to effectively perform disruption of an ldh gene as a target, a homologous recombination method is preferable. Since all of these methods are the technique which has been per se previously established sufficiently, such disruption in the present invention may be performed according to them.

Preparation of an ldh gene-disrupted strain of a coryneform bacterium by a homologous recombination method will be described in detail in Examples, and can be usually performed by the following operation method and procedure.

A) Extraction of DNA from microorganisms used in the present invention; A method of extracting a genomic DNA from a coryneform bacterium can be performed by a method of Sambrook et al. (Sambrook, J., E. F. Fritsch and T. Maniatis, 1989, Molecular cloning: a laboratory manual, 2nd ed. Cold Spring Harbor Laboratory Press, Cold Spring Harbor, N.Y.) except that bacterial cells are treated with lysozyme having a concentration of 4 mg/ml at 37° C. for 30 minutes in advance.

B) Cloning of an ldh gene as a target and production of a plasmid for disruption; Cloning of an ldh gene can be performed by a PCR method using primers designed from amino acid sequences conserved between the known ldh genes, or hybridization using the known ldh gene and, as the most effective method, primers are designed from a genomic sequence (in the case of *Corynebacterium glutamicum* R strain, an entire genome sequence (see Hiroshi Nonaka, Kaori Nakata, Naoko Okai, Mariko Wada, Yumiko Sato, Kos Peter, Masayuki Inui, and Hideaki Yukawa "*Corynebacterium glutamicum* R Genome Analysis", Japan Society for Bioscience, Biotechnology, and Agrochemistry, April, 2003 Yokohama, Year 2003 Meeting, Abstract, p. 20) has been determined, and this can be utilized), and a gene containing a full-length ldh gene can be amplified and obtained by PCR using a genomic DNA of a coryneform bacterium as a template. On the other hand, in the preparation of a disrupted strain of an ldh gene, an ldh gene amplified by PCR is cloned into an *Escherichia coli* vector such as pHSG398 which can not be replicated in a coryneform bacterium, and a plasmid for disrupting a gene is prepared, wherein a drug (e.g. kanamycin, etc.) resistant gene (used as a marker gene upon disruption of a gene) is inserted into a unique restriction enzyme site situated approximately at the center of an ldh gene.

C) A homologous recombination method by plasmid introduction; Preparation of an ldh gene-disrupted strain can be performed by introducing the plasmid for disrupting a gene into a cell by a method of effectively introducing a gene into a coryneform bacterium (electric pulse method (Y. Kurusu, et al., Agric. Biol. Chem. 54: 443-447. 1990. and A. A. Vertes, et al., Res. Microbiol. 144: 181-185. 199)), and disrupting (or inactivating) an ldh gene by homologous recombination into a chromosome. Disruption of the ldh gene can be confirmed at a gene level by PCR or a Southern hybridization method, or by insertion of a marker gene fragment such as a kanamycin-resistant gene in addition to an ldh gene fragment into a chromosome, or at a protein level by loss of enzyme activity of lactate dehydrogenase.

The thus prepared coryneform bacterium ldh-disrupted strain is further transformed for highly expressing a PC gene. That is, a nucleic acid fragment containing a gene sequence encoding an enzyme having PC activity is introduced into the aforementioned coryneform bacterium ldh-disrupted strain, thereby to transform the bacterium in order to more highly express PC activity as compared with an ldh-disrupted strain before introduction.

A method of introducing a nucleic acid fragment containing a PC gene will be descried in Examples in detail, and a nucleic acid fragment containing a PC gene used for the purpose of the object of the invention is widely present on a chromosome of microorganisms, animals and plants, the fragment may be possessed by a coryneform bacterium itself of the present invention, or may be heterogonous.

Alternatively, if a base sequence thereof is known, a gene synthesized according to the sequence may be used. Even when a gene sequence is unknown, an enzyme protein is purified using PC activity as an index, and a nucleic acid fragment can be isolated from its N-terminal amino acid sequence or partial degraded sequence by a conventional hybridization procedure. Alternatively, a fragment can be obtained by hybridization or a PCR method based on an amino acid sequence conserved between PC enzyme proteins. A base sequence of the obtained fragment can be determined by a conventional procedure.

As a PC enzyme protein or a gene whose property has been revealed, there are exemplified as follows:

*Corynebacterium glutamicum* (*C. glutamicum*); (GenBank Y09548) human; (GenBank K02282; S. Freytag et al., J. Biol. Chem., 259, 12831-12837 (1984)),

*Saccharomyces cerevisiae* (*S. cerevisiae*); (GenBank X59890, J03889, and M16595; R. Stucka et al., Mol. Gen. Genet., 229, 305-315 (1991); F. Lim et al., J. Biol. Chem., 263, 11493-11494 (1988); D. Myers et al., Biochemistry, 22, 5090-5096 (1983)),

*Rhizobium etli* (*R. etli*); (GenBank U51439; M. Dunn et al., J. Bacteriol., 178, 5960-5070 (1996)),

*Schizosaccharomyces pombe* (*S. pombe*); (GenBank D78170),

*Bacillus stearothermophilus* (*B. stearothermophilus*); (GenBank D83706; H. Kondo, Gene, 191, 47-50 (1997); S. Libor, Biochemistry, 18, 3647-3653 (1979)), and

*Pseudomanas fluorescens* (*P. fluorescens*); (R. Silvia et al, J. Gen. Microbiol., 93, 75-81 (1976)).

The PC gene of the present invention may be such that a part of a base sequence is substituted with other base, or deleted, or a base may be newly inserted, or further a part of a nucleotide sequence may be translocated, as far as PC activity is retained. All of these derivatives can be used in the present invention. The aforementioned "part" may be, for example, one to several in terms of amino acid residues number.

A nucleic acid fragment containing the PC gene of the present invention is introduced into the aforementioned coryneform bacterium ldh-disrupted strain under a control sequence under which a PC gene can be expressed, using a plasmid vector. Herein, "under control sequence" means that a PC gene can be autonomously replicated by cooperative work with, for example, a promoter, an inducer, an operator, a ribosome binding site and a transcription terminator. A plasmid vector used for such purpose may be any plasmid vector as far as it contains a gene which commands autonomous replicating function in a coryneform bacterium ldh-disrupted strain. Examples of the plasmid vector include pAM330 (Agric. Biol. Chem., vol. 48, 2901-2903 (1984) and Nucleic Acids Symp Ser., vol. 16, 265-267 (1985)) (derived from *Brevibacterium lactofermentum* 2256), pHM1519 (Agric. Biol. hem., vol. 48, 2901-2903 (1984)) (derived from *Corynebacterium glutamicum* ATCC 13058), pCRY30 (Appl. Environ. Microbiol., vol. 57, 759-764 (1991)), pEK0, pEC5, pEKEx1 (Gene, vol. 102, 93-98 (1991)) and pCG4 (J. Bacteriol., vol. 159, 306-311 (1984)) (derived from *Corynebacterium gluatmicum* T250).

For constructing a plasmid used in generating the coryneform bacterium transformant of the present invention, for example, when a PC gene derived from *Corynebacterium glutamicum* R strain is used, a plasmid can be constructed by ligating a 3.8-kb gene fragment containing an entire PC gene (which can be amplified by PCR based on the result of entire genome analysis of *Corynebacterium glutamicum* R strain (see Hiroshi Nonaka, Kaori Nakata, Naoko Okai, Mariko Wada, Yumiko Sato, Kos Peter, Masayuki Inui, and Hideaki Yukawa "*Corynebacterium glutamicum* R Genome Analysis", Japan Society for Bioscience, Biotechnology, and Agrochemistry, April, 2003, Yokohama, Year 2003 Meeting, Abstract, p. 20) (details are described in Examples) with a suitable control sequence such as a promoter, a terminator and the like, and inserting this into a suitable restriction enzyme site of any one of plasmid vectors exemplified above.

Examples of a promoter for expressing a PC gene in the aforementioned recombinant plasmid include a promoter originally possessed by a coryneform bacterium, but are not limited to it, and any promoter can be used as far as it is a base sequence having the function of initiating transcription of a PC gene. In addition, examples of a terminator under control sequence disposed downstream of a PC gene include a terminator originally possessed by a coryneform bacterium, but is not limited to it and, for example, any terminator can be used as far as it is a base sequence having the function of terminating transcription of a PC gene such as a terminator of tryptophan operon derived from *Escherichia coli*.

A method of introducing a plasmid vector containing a PC gene into a coryneform bacterium ldh-disrupted strain is not particularly limited as far as it is a method which can introduce a PC gene into a coryneform bacterium ldh-disrupted strain such as an electric pulse method (electroporation method) and a $CaCl_2$ method.

As an embodiment thereof, for example, an electric pulse method can be used according to the known method Agric. Biol. Chem., vol. 54, 443-447 (1990), Res. Microbiol., vol. 144, 181-185 (1993)).

As a method of obtaining the generated coryneform bacterium transformant of the present invention, according to a conventional method, a transformed coryneform bacterium can be selected by incorporating also a drug resistant gene into a plasmid vector containing a PC gene, and coating the coryneform bacterium of the present invention which has been subjected to PC gene introduction treatment, on a plate medium containing a suitable concentration of the drug. As an embodiment thereof, for example, a method described in Agric. Biol. Chem., vol. 54, 443-447 (1990), Res. Microbiol. vol. 144, 181-185 (1993) can be used.

The thus generated coryneform bacterium of the present invention in which an ldh gene has been disrupted, and a PC gene has been transformed so as to be highly expressed has been deposited at Independent Administrative Agency, Industrial Technical Comprehensive Laboratory Patent Organism Depositary Center with accession number: FERM BP-10060 under a bacterium name; *Corynebacterium glutamicum* R ldh⁻/pCRB1-PC.

Occasionally and additionally, an anaplerotic pathway enzyme gene contributing to improvement in the rate of producing dicarboxylic acids of the present invention, or fumarate reductase (FRD) gene contributing to the tricarboxylic acid cycle may be introduced into *Corynebacterium glutamicum* R ldh⁻/pCRB1-PC. As an example of such coryneform bacterium of the present invention, a bacterium has been deposited at Independent Administrative Agency, Industrial Technical Comprehensive Laboratory Patent Organism Depositary Center with accession number: FERM BP-10061 under a bacterium name; *Corynebacterium glutamicum* R ldh⁻/pCRB1-PC-FRD.

The thus generated coryneform bacterium of the present invention can produce dicarboxylic acids, for example, succinic acid, fumaric acid or malic acid at a high production rate using saccharides as a raw material, in a reaction solution containing carbonate, bicarbonate ions or carbon dioxide gas under the particular reducing state, in other words, in a reaction solution containing one member or a mixture of two or more members selected from the group consisting of carbonate ion, bicarbonate ion and carbon dioxide gas.

In a process for producing dicarboxylic acids of the present invention, first, an aerobic coryneform bacterium generated by transformation by the aforementioned process of the present invention is grown and cultured under the aerobic condition.

Culturing of the aerobic coryneform bacterium of the present invention can be performed using a conventional nutrient medium containing carbon sources, nitrogen sources and inorganic salts. For culturing, as carbon sources, for example, glucose or molasses can be used and, as nitrogen sources, for example, ammonia, ammonium sulfate, ammonium chloride, ammonium nitrate and urea can be used alone or in combination thereof. In addition, as inorganic salts, for example, potassium monohydrogen phosphate, potassium dihydrogen phosphate or magnesium sulfate can be used. Besides, if necessary, nutrients such as peptone, meat extract, yeast extract, corn steep liquor, casamino acid, or various vitamins such as biotin and thiamine can be appropriately added.

Culturing can be performed usually at a temperature of about 20° C. to about 40° C., preferably about 25° C. to about 35° C., under aerobic condition such as aeration stirring or shaking. The pH at culturing is suitably in a range of about 5 to 10, preferably about 7 to 8, and the pH during culturing can be adjusted by adding acidic or alkaline compounds. The concentration of carbon sources at culturing initiation is about 1 to 20% (w/v), preferably about 2 to 5% (w/v). In addition, the culturing duration is usually about 1 to 7 days.

Then, cultured cells of the aerobic coryneform bacterium of the present invention are recovered. A method of recovering and separating cultured cells from the culture obtained above is not particularly limited, but the known method such as centrifugation and membrane separation can be used.

The recovered cultured cells can be additionally treated, and the resulting treated cells may be used in the subsequent step of producing dicarboxylic acids. A cell treating method may be a method wherein some treatment is added to cultured cells, and examples include a method of immobilizing bacterial cells with acrylamide or carrageenan.

Then, cultured cells of the aerobic coryneform bacterium of the present invention recovered and separated from the culture obtained above, or treated cells thereof are subjected to a desired dicaroxylic producing reaction in a reaction medium under the reducing state. As a manner of producing dicarboxylic acids, it may be possible to adopt any one of a batch method and a continuous method.

In a biochemical reaction under the reducing state in the present invention, growth and division of the aerobic coryneform bacterium of the present invention is suppressed, and substantially complete suppression of the secreted byproduct accompanied with the growth can be realized. From this point of view, when the cultured and recovered coryneform bacterium or treated cells thereof is supplied to a reaction medium, it is recommended to use a method or the condition in which the surrounding condition at culturing in and outside the coryneform bacterium cell is not reflected in a reaction medium. That is, it is preferable that a reaction medium does not substantially contain a produced substance which is produced during growth and culturing, and is present in and outside bacterial cells. More specifically, there is recommended a state where a secreted byproduct which is produced during growth and culturing, and is released outside of the cells, and a substance which is produced by the aerobic metabolism function in cultured cells, and remains in cells is not substantially present in a reaction medium. Such condition is realized by a method of centrifugation or membrane separation of the culture solution after the growth and culturing and/or by allowing cells after culturing to stand under the reducing state for about 2 hours to 10 hours.

In the present step, a reaction medium under the reducing state is used. A reaction medium may have any state such as solid, semisolid and liquid as far as under the reducing state. One essential feature of the present invention is to perform a biochemical reaction due to the metabolism function of the coryneform bacterium under the reducing state to produce desired dicarboxylic acids.

The reducing state in the present invention is defined by an oxidation-reduction potential of a reaction system, and an oxidation-reduction potential of a reaction medium is preferably about −200 mV to about −500 mV, more preferably about −250 mV to about 500 mV. The reducing state of a reaction medium can be presumed to some extent, simply by a resazurin indicator (in the reducing state, discoloration from blue to colorless) and, precisely, an oxidation-reduction potentiometer (e.g. ORP Electrodes manufactured by BROADLEY JAMES) is used. In the preset invention, it is preferable that the reducing state is maintained from the instant time immediately after addition of bacterial cells or treated bacterial cells to a reaction medium to the time of collection of dicarboxylic acids, but at least at the time of collection of dicarboxylic acids, a reaction medium should be in the reducing state. It is desirable that a reaction medium is retained in the reducing state for about 50% or longer, more preferably about 70% or longer, further preferably about 90% or longer of duration of the reaction time. Inter alia, it is desirable that an oxidation-reduction potential of a reaction medium is retained at about −200 mV to about −500 mV for about 50% or longer, more preferably about 70% or longer, further preferably about 90% or longer of duration of a reaction time.

Such reducing state is specifically realized by the hereinbefore mentioned method of preparing cultured bacterial cells after culturing, a method of adjusting a reaction medium, or a method of maintaining the reducing state during the reaction.

As a method of adjusting a reaction medium under the reducing state, the known method may be used. For example, regarding a method of adjusting an aqueous solution for a reaction medium, a method of adjusting a culturing solution for an absolute anaerobic microorganism such as a sulfate-reducing microorganism (Pfennig, N et. al. (1981): The dissimilatory sulfate-reducing bacteria, In The Prokaryotes, A Handbook on Habitats, Isolation and Identification of Bacteria, Ed. by Starr, M. P. et al., p. 926-940, Berlin, Springer Verlag. and "Agricultural and Horticultural Chemistry Experimental Book, vol. 3, edited by Kyoto University, Faculty of Agriculture, Agricultural and Horticultural Chemistry Section, 1990, 26th print, published by Sangyotosho") can be referenced, and by such ways, the desired aqueous solution in the reducing state can be obtained.

More specifically, examples of a method of adjusting an aqueous solution for a reaction medium include a method of removing a dissolved gas by heat-treating or reduced pressure-treating an aqueous solution for a reaction medium.

More specifically, an aqueous solution for a reaction medium under the reducing state can be prepared by removing a dissolved gas, particularly, dissolved oxygen by treating an aqueous solution for a reaction medium for about 1 to 60 minutes, preferably about 5 to 40 minutes under reduced pressure of about 10 mmHg or lower, preferably about 5 mmHg or lower, more preferably about 3 mmHg or lower. Alternatively, an aqueous solution of a reaction medium under the reducing state may be adjusted by adding a suitable reducing agent (e.g. thioglycolic acid, ascorbic acid, cysteine hydrochloride salt, mercaptoacetic acid, thiolacetic acid, glutathione and sodium sulfide). Alternatively, occasionally, appropriate combination of these methods may be an effective method of adjusting an aqueous solution for a reaction medium under the reducing state.

As a method of maintaining the reducing state during the reaction, it is desirable to prevent incorporation of oxygen from the outside of a reaction system as much as possible, and a method of sealing a reaction system with an inactive gas such as nitrogen gas and carbon dioxide gas is usually used. As a method of effectively preventing incorporation of oxygen, in order to effectively function the metabolism function in cells of the coryneform bacterium of the present invention during the reaction, and when it becomes necessary to appropriately add a pH maintaining adjusting solution for a reaction system or add various nutrients-dissolved solution in some cases and, in such case, it is effective to remove oxygen from a solution to be added in advance.

As a factor influencing on an oxidation-reduction potential of a reaction system, a kind and a concentration of a reaction system atmosphere gas, a reaction temperature, a pH of a reaction solution, and a concentration and a composition of inorganic and organic various compounds to be used for producing desired dicarboxylic acids are contemplated. An oxidation-reduction potential of a reaction medium in the present invention shows integrating results of the aforementioned various influencing factors.

A reaction medium contains saccharides which are to be a raw material for producing dicarboxylic acids, and carbonate or bicarbonate ions.

Examples of the saccharide include monosaccharide such as glucose, galactose, fructose and mannose, disaccharide such as cellobiose, sucrose, lactose and maltose, and polysaccharide such as dextrin and soluble starch. Inter alia, glucose is preferable. In this case, glucose is used in a concentration range of about 0.5 to 500 g/L (liter).

Carbonate or bicarbonate ions are supplied from carbonic acid or bicarbonic acid or salts thereof, or carbon dioxide gas. Examples of the salt of carbonic acid or bicarbonic acid include ammonium carbonate, sodium carbonate, potassium carbonate, ammonium bicarbonate, sodium bicarbonate, and potassium bicarbonate. The carbonate or bicarbonate ions are used in a concentration range of about 1 to 500 mM, preferably about 2 to 300 mM. When carbon dioxide gas is supplied, it is supplied so that it is contained in a solution at a concentration of about 50 mg/L to 25 g/L, preferably about 100 mg/L to 15 g/L.

A reaction medium composition used in a reaction of producing dicarboxylic acids contains necessary components for the coryneform bacterium or treated bacterium thereof to maintain its metabolism function, that is, in addition to carbon sources such as various saccharides, and carbonic acid sources, the medium composition contains nitrogen sources necessary for protein synthesis (e.g. ammonia, ammonium sulfate, ammonium chloride, ammonium nitrate and urea), salts of phosphorus, potassium or sodium, and minor metal salts of iron, manganese or calcium. An amount of them to be added can be appropriately determined depending on a necessary reaction time, a kind of desired dicarboxylic acid product, and a kind of the coryneform bacterium to be used. Depending on the coryneform bacterium used, it is preferable to add specific vitamins in some cases. A reaction of the aerobic coryneform bacterium or treated cells thereof with saccharides is preferably performed under such temperature condition that the aerobic coryneform bacterium of the present invention or treated cells thereof can act, and can be appropriately selected depending on a kind of the aerobic coryneform bacterium or treated cells thereof (for detail, see Examples).

The dicarboxylic acids produced in a reaction medium as described above are collected. As a method therefor, the known method which is used in a bioprocess can be used. Examples of such known method include a salting out method, a recrystallization method, an organic solvent extraction method, an esterification distillation separating method, a chromatographic separating method and an electrodialysis method for dicarboxylic acid product solution, and the methods of these separation, purification and collection can be appropriately determined depending on the property of dicarboxylic acids.

EXAMPLES

The present invention will be explained below by Examples, but the present invention is not limited to such the Examples. Unless otherwise indicated, "%" indicates "% by weight".

Example 1

Preparation of ldh Gene-disrupted Strain of *Corynebacterium glutamicum* R Strain (Independent Administrative Agency, Industrial Technical Comprehensive Laboratory Patent Organism Depositary Center with Accession Number: FERM P-18976)

(A) Extraction of Total DNA from *Corynebacterium glutamicum* R Strain

A wild strain *Corynebacterium glutamicum* R was inoculated to 1 L of a medium A (composition: urea: 2 g, $(NH_4)_2SO_4$: 7 g, $KH_2PO_4$: 0.5 g, $K_2HPO_4$: 0.5 g, $MgSO_4.7H_2O$: 0.5 g, $FeSO_4.7H_2O$: 6 mg, $MnSO_4.nH_2O$: 4.2 mg, D-biotin: 200 μg, thiamine hydrochloride: 200 μg, yeast extract 2 g, casamino acid 7 g, glucose 20 g and distilled water: 1000 ml (pH 6.6)) using a platinum loop, and this was cultured at 33° C. to the late logarithmic growth phase, and then bacterial cells were collected.

The resulting bacterial cells were suspended in 15 ml of a solution containing respective components of 10 mg/ml lysozyme, 10 mM NaCl, 20 mM Tris buffer (pH 8.0) and 1 mM EDTA.2Na (the concentration of each component is a final concentration) to a concentration of 10 mg/ml. Then, proteinase K was added to a final concentration of 100 μg/ml, and the mixture was maintained at 37° C. for 1 hour. Further, sodium dodecylsulfate (SDS) was added to a final concentration of 0.5%, and the temperature was retained at 50° C. for 6 hours to lyse bacterial cells. An equivalent amount of a phenol/chloroform solution was added to this lysed cells solution, this was shaken gently at room temperature for 10 minutes, the whole solution was centrifuged (5,000×g, 20 min, 10 to 12° C.), and the supernatant fraction was obtained. Sodium acetate was added to this supernatant to 0.3 M, and a 2-fold amount of ethanol was added slowly. A DNA present between an aqueous layer and an ethanol layer was wound with a glass bar, and this was washed with 70% ethanol, and dried in the air. 10 mM Tris buffer (pH 7.5)–1 mM EDTA.2Na solution (5 ml) was added to the resulting DNA, and this was allowed to stand at 4° C. overnight, and used in a later experiment.

(B) Cloning of ldh Gene and Generation of Plasmid for Disrupting Gene

Using the chromosome DNA prepared in the above (A) as a template, PCR was performed.

Regarding PCR, in order to clone an ldh gene, based on results of entire genome analysis of *Corynebacterium glutamicum* R strain (see Hiroshi Nonaka, Kaori Nakata, Naoko Okai, Mariko Wada, Yumiko Sato, Kos Peter, Masayuki Inui, and Hideaki Yukawa "*Corynebacterium glutamicum* R Genome Analysis", Japan Society for Bioscience, Biotechnology, and Agrochemistry, April, 2003 Yokohama, Year 2003 Meeting, Abstract, p. 20), the following one pair of primers were synthesized using "394 DNA/RNA synthesizer" manufactured by Applied Biosystems, and used.

Primers for amplifying ldh gene

```
ldh-N; 5'-CTCTGTCGACATCAGGAAGTGGGATC (SEQ ID NO: 1)
       GAAA-3', ldh-C; 5'-CTCTGTCGACTTCCATCCAACAGTTT (SED ID NO: 2)
       CATT-3'
```

In any primer, a SalI site is added to a terminus.

PCR was performed under the following condition using TaKaRa Ex Taq) (manufactured by TAKARA SHUZO Co., Ltd.) as a reaction reagent using "DNA Thermal Cycler" manufactured by Perkin Elmer Cetus.

Reaction solution:
(10×)PCR buffer: 10 μl
1.25 mM dNTP mixed solution: 16 μl
Template DNA 10 μl (DNA content: 1 μM or less)
Aforementioned two kinds of primers: Each 1 μl (final concentration 0.25 μM)
TaKaRa Example Tax DNA polymerase: 0.5 μl
Sterile distilled water: 61.5 μl
Above components were mixed, and 100 μl of this reaction solution was subjected to PCR.

PCR Cycle:
Denaturation process: 94° C., 60 seconds
Annealing process: 52° C., 60 seconds
Extension process: 72° C., 120 seconds
The above is one cycle, and 30 cycles were performed.

The above-obtained reaction solution (10 μl) was electrophoresed on a 0.8% agarose gel and, in the case of an ldh gene, about 1.1 kb of a DNA fragment could be detected.

Then, 10 μl of 1.1 kb of the PCR product containing the ldh gene and 2 μl of a plasmid pHSG398 (manufactured by TAKARA SHUZO Co., Ltd.) containing a chloramphenicol resistant gene were cut with a restriction enzyme SalI, respectively, the restriction enzyme was inactivated by treatment at 70° C. for 10 minutes, both were mixed, respective components of 1 μl of T4 DNA ligase 10×buffer and 1 unit of T4DNA ligase were added thereto, and sterile distilled water was added to 10 μl to react them at 15° C. for 3 hours. This ligation solution was used to transform *Escherichia coli* JM109 (manufactured by TAKARA SHUZOU Co., Ltd.) by a calcium chloride method (Journal of Molecular Biology, 53, 159 (1970)), and this was smeared on a medium (10 g of tryptone, 5 g of yeast extract, 5 g of NaCl and 16 g of agar were dissolved in 1 L of distilled water) containing 50 mg of chloramphenicol, 200 mg of X-gal (5-Bromo-4-chloro-3-indoxyl-beta-D-galactopyranoside) and 100 mg IPTG (isopropyl 1-thio-beta-d-galactoside).

The growing strain exhibiting white spot on the above medium was selected and cultured in a liquid medium by a conventional method, and a plasmid DNA was extracted from the cultured solution and cut with a restriction enzyme SalI, thereby to confirm an inserted fragment. As a result, in addition to a plasmid pHSG398 as a DNA fragment of about 2.2 kb, an inserted DNA fragment of a length of about 1.1 kb containing an ldh gene was recognized.

The plasmid containing the ldh gene was designated as pHSG398-LDH.

At the approximately center of the ldh gene contained in this plasmid pHSG398-LDH, a restriction enzyme site EcoRV (only one place in the present plasmid) is present. 10 μl of a DNA solution of the above-extracted plasmid pHSG398-LDH was completely cut with EcoRV, and treated at 70° C. for 10 minutes to inactivate a restriction enzyme.

On the other hand, 2 μl of a plasmid pUC4K (manufactured by Pharmacia) was cut with a restriction enzyme PstI and separated by agarose electrophoresis, and a DNA fragment containing about 1.2 kb PstI kanamycin-resistant gene was excised from a gel, followed by purification. This purified 1.2 kb PstI kanamycin-resistant gene DNA fragment was blunt end-treated with a DNA blunting kit (manufactured by TAKARA SHUZOU Co., Ltd.).

The EcoRV-cut pHSG398-LDH DNA solution and the blunt end-treated 1.2 kb PstI kanamycin-resistant gene DNA solution were mixed, respective components of 1 μl of T4 DNA ligase 10×buffer and 1 unit of a T4 DNA ligase were added thereto, sterile distilled water was added to 10 μl, and components were reacted at 15° C. for 3 hours. This ligation solution was used to transform *Escherichia coli* JM109 (manufactured by TAKARA SHUZOU Co., Ltd.) by a calcium chloride method (Journal of Molecular Biology, 53, 159 (1970)), and this was smeared on a medium (10 g of tryptone 5 g of yeast extract, 5 g of NaCl and 16 g of agar were dissolved in 1 L of distilled water) containing 50 mg of kanamycin.

The growing strain on the medium was selected and cultured in a liquid medium by a conventional method, and a plasmid DNA was extracted from the cultured solution, and cut with a restriction enzyme SalI to confirm an inserted fragment. As a result, in addition to a DNA fragment of a plasmid pHSG398 of about 2.2 kb, an inserted DNA fragment of a length of about 2.3 kb containing a kanamycin-resistant gene at the center of the ldh gene was recognized. This plasmid was designated as pHSG398-LDH/Km.

(C) Generation of ldh Gene-Disrupted Strain

The plasmid pHSG398 and its derivative, the plasmid pHSG398-LDH/Km obtained in the above (B) are a plasmid which can not be replicated in the genus *Corynebacterium* (including *Corynebacterium glutamicum* R strain). According to an electric pulse method Y. Kurusu, et al., Agric. Biol. Chem. 54: 443-447. 1990 and A. A. Vertes, et al., Res. Microbiol. 144: 181-185, 1993), the plasmid pHSG398-LDH/Km was introduced into *Corynebacterium glutamicum* R strain, and this was coated on an agar medium A (1 L)

(composition:urea:2 g, $(NH_4)_2SO_4$: 7 g, $KH_2PO_4$: 0.5 g, $K_2HPO_4$: 0.5 g, $MgSO_4.7H_2O$: 0.5 g, $FeSO_4.7H_2O$: 6 mg, $MnSO_4.nH_2O$: 4.2 mg, D-biotin: 200 µg, thiamine hydrochloride: 200 µg, yeast extract: 2 g, casamino acid: 7 g, glucose: 20 g, agar: 16 g were dissolved in 1000 ml of distilled water (pH6.6)) containing 50 µg/ml of kanamycin.

The growing strain which was grown on the agar medium A containing 50 µg/ml kanamycin, when a plasmid pHSG398-LDH/Km caused one point homologous recombination with a wild type ldh gene on a chromosome, exhibits chloramphenicol resistance due to expression of a chloramphenicol resistance gene on the vector pHSG398, and kanamycin-resistance due to expression of a kanamycin resistance gene in the ldh gene, while when caused a two point homologous recombination, the strain exhibits chloramphnicol sensitivity since a chloramphenicol resistance gene on a vector pHSG398 is dropped out, and kanamycin resistance due to expression of a kanamycin resistance gene in the ldh gene. Therefore, the objective ldh gene-disrupted strain exhibits chloramphenicol sensitivity and kanamycin resistance.

The grown strain which had exhibited chloramphenicol sensitivity and kanamycin resistance was cultured in a liquid medium, and a chromosome DNA was extracted from the culture solution, and disruption of the ldh gene on a chromosome was confirmed by genomic Southern hybridization described below. The chromosome DNA was degraded with a suitable restriction enzyme, blotted on a nylon filter (Hybond N; manufactured by Amersham), labeled by a DIG system (manufactured by Boehringer) using a 1.1 kb PCR product containing the LDH gene obtained in the above (B) as a probe, and genomic Southern hybridization was performed. As compared with a pattern of genomic Southern hybridization using a chromosome DNA extracted from a wild strain, a band longer by the 1.2 kb kanamycin-resistant gene shown in the above (B) was detected in a pattern of the gene-disrupted strain, and construction of the ldh gene on a chromosome could be confirmed. The thus obtained ldh gene-disrupted strain was named as *Corynebacterium glutamicum* R ldh$^-$ strain.

Loss of the ldh activity in *Corynebacterium glutamicum* R ldh$^-$ strain was confirmed by the following method.

The *Corynebacterium glutamicum* R ldh$^-$ strain was inoculated on 100 ml of a medium A (1 L) (composition: urea: 2 g, $(NH_4)_2SO_4$: 7 g, $KH_2PO_4$: 0.5 g, $K_2HPO_4$: 0.5 g, $MgSO_4.7H_2O$: 0.5 g, $FeSO_4.7H_2O$: 6 mg, $MnSO_4.nH_2O$: 4.2 mg, D-biotin: 200 µg, thiamine hydrochloride: 200 µg, yeast extract: 2 g, casamino acid: 7 g, glucose: 20 g and distilled water: 1000 ml (pH 6.6)) using a platinum loop, and this strain was cultured at 33° C. until the late stage of logarithmic growth phase, and then bacterial cells were collected. The bacterial cells were washed once with a Tris buffer (100 mM Tris-HCl (pH 7.5), 20 mM KCl, 20 mM $MgCl_2$, 5 mM $MnSO_4$, 0.1 mM EDTA, 2 mM DTT). 0.5 g of the washed bacterial cells were suspended in 2 ml of the same buffer, and disrupted bacterial cells were obtained using an ultrasonicator (Astrason model XL2020) under ice-cooling. The disrupted cells were centrifuged (10,000×g, 4° C., 30 min), and the supernatant was obtained as a crude enzyme solution. As a control, a crude enzyme solution of wild type *Corynebacterium glutamicum* R strain was similarly prepared, and was subjected to the following activity measurement. Measurement of ldh activity was performed by a method of measuring an amount of a coenzyme NADH which is oxidized to NAD$^+$ accompanied with lactic acid production using pyruvic acid as a substrate in terms of change in an absorbance at 340 nm (Bunch, P. K., F. Mat-Jan, N. Lee, and D. P. Clark. 1997. The ldhA gene encoding the fermentative lactate dehydrogenase of *Escherichia coli*. Microbiology 143:187-195.). As a result, since ldh activity in the *Corynebacterium glutamicum* R ldh$^-$ was not detected, disruption of the ldh gene was confirmed.

Example 2

Generation of PC Gene High Expression Recombinant of *Corynebacterium glutamicum* R ldh$^-$ Strain (A) Construction of Coryneform Bacterium—*Escherichia coli* Shuttle Vector pCRB1

A DNA fragment containing ORF1 (rep) of a plasmid pAM330 Yamaguchi, R. et al., Agric. Biol. Chem. 50, 2771-2778(1986), (Japanese Patent Application Laid-Open No. 58-67679) present in *Brevibacterium lactofermentum* ATCC 13869 was amplified by the following PCR method.

Upon PCR, the following one pair of primers were synthesized using "394 DNA/RNA synthesizer" manufactured by Applied Biosystems, and were used.

Primers for amplifying ORF1 (rep) gene

```
Rep-N; 5'-CTCTGTTAACACAACAAGACCCATCA (SEQ ID NO: 3)
       TAGT-3',

Rep-C; 5'-CTCTGTTAACACATGCAGTCATGTCG (SEQ ID NO: 4)
       TGCT-3'
```

In any primer, a HpaI site is added to a terminus.

As a template DNA, a plasmid pAM330 was used.

PCR was performed under the same conditions as those of Example 1(B).

10 µl of the reaction solution produced above was electrophoresed on a 0.8% agarose gel, and a DNA fragment of about 1.8 kb containing a Rep gene could be detected.

On the other hand, upon construction of coryneform bacterium-*Escherichia coli* shuttle vector, in order to retain a lac Zα gene and its inside multicloning site of an *Escherichia coli* vector pHSG398 (manufactured by TAKARA SHUZO Co., Ltd.) containing a chloramphenicol resistance gene, pHSG398 was amplified so that an EcoRV site was newly added by PCR.

Upon PCR, the following one pair of primers were synthesized using "394 DNA/RNA synthesizer" manufactured by Applied Biosystems, and were used.

Primers for amplifying plasmid pHSG398

```
398-N; 5'-CTCTGATATCGTTCCACTGAGCGTCA (SEQ ID NO: 5)
       GACC-3',

398-C; 5'-CTCTGATATCTCCGTCGAACGGAAGA (SEQ ID NO: 6)
       TCAC-3'
```

In any primer, an EcoRV site is added to a terminus.

As a template DNA, a plasmid pHSG398 was used.

PCR was performed under the same conditions as those of Example 1(B).

10 µl of the reaction solution produced above was electrophoresed on a 0.8% agarose gel, and a DNA fragment of about 2.2 kb containing a full length plasmid pHSG398 could be detected.

Then, 5 µl of a DNA fragment of about 1.8 kb containing the Rep gene cut with HpaI and a DNA fragment of about 2.2 kb containing a full length plasmid pHSG398 cut with EcoRV were mixed, respective components of 1 µl of T4 DNA ligase 10× buffer, and 1 unit of T4 DNA ligase were added thereto, sterile distilled water was added to 10 µl, and the mixture was reacted at 15° C. for 3 hours to bind both DNA fragments.

Using the resulting plasmid mixed solution, *Escherichia coli* JM109 (manufactured by TAKARA SHUZO Co., Ltd.) was transformed by a calcium chloride method (Journal of Molecular Biology, 53, 159 (1970)), and this was smeared on a medium (10 g of tryptone, 5 g of yeast extract, 15 g of NaCl and 16 g of agar were dissolved in 1 L of distilled water) containing 50 mg of chloramphenicol.

The grown strain on this medium was liquid-cultured by a conventional method, a plasmid DNA was extracted from the culture solution, the plasmid was cut with a restriction enzyme, and inserted fragment was confirmed. As a result, in addition to a plasmid pHSG398 DNA fragment of 2.2 kb, an inserted DNA fragment of a length of about 1.8 kb was recognized.

This coryneform bacterium-*Escherichia Coli* shuttle vector is described as pCRB1.

(B) Cloning of PC Gene and Generation of Recombinant

Using a chromosome DNA prepared in Example 1(A) as a template, PCR was performed.

Upon PCR, in order to clone a PC gene, based on results of entire genome analysis of *Corynebacterium glutamicum* R strain ((see Hiroshi Nonaka, Kaori Nakata, Naoko Okai, Mariko Wada, Yumiko Sato, Kos Peter, Masayuki Inui, Hideaki Yukawa "*Corynebacterium glutamicum* R Genome Analysis", Japan Society for Bioscience, Biotechnology, and Agrochemistry, April, 2003 Yokohama, Year 2003 Meeting, Abstract, p. 20), the following one pair of primers were synthesized using "394 DNA/RNA synthesizer" manufactured by Applied Biosystems, and were used.

Primers for amplifying PC gene

```
PC-N; 5'-CTCTACATGTTGCAGGTCAGAGGAGT (SEQ ID NO: 7)
      GT-3',

PC-C; 5'-CTCTGCATGCAGGAATCGTGTGCATG (SEQ ID NO: 8)
      GTC-3'
```

In the former, a NspI site and, in the latter, SphI site are added to a terminus, respectively.

As a template DNA, a genomic DNA of *Corynebacterium glutamicum* R strain extract in the above (A) was used.

PCR was performed under the same conditions as those of Example 1(B).

10 µl of the reaction solution produced above was electrophoresed on a 0.8% agarose gel and, in the case of a PC gene, a DNA fragment of about 3.8 kb could be detected.

Then, 10 µl of the 3.8 kb PCR product containing a DC gene which had been cut with restriction enzymes NspI and SphI, and 2 µl of the coryneform bacterium-*Escherichia coli* shuttle vector pCRB1 constructed in the above (A) which had been cut with a restriction enzyme SphI were treated at 70° C. for 10 minutes, respectively, to inactivate restriction enzymes, and both were mixed. Respective components of 1 µl of T4 DNA ligase 10× buffer, and 1 unit of T4 DNA ligase were added thereto, and sterile distilled water was added to an amount of 10 µl, followed by the reaction at 15° C. for 3 hours. Using this ligation solution, *Escherichia coli* JM109 (manufactured by TAKARA SHUZO Co., Ltd.) was transformed by a calcium chloride method (Journal of Molecular Biology, 53, 159 (1970)), and this was smeared on a medium (10 g of tryptone, 5 g of yeast extract, 15 g of NaCl and 16 g of agar were dissolved in 1 L of distilled water) containing 50 mg of chloramphenicol, 200 mg of X-gal (5-Bromo-4-chloro-3-indoxyl-beta-D-galactopyranoside), and 100 mg of IPTG (isopropyl 1-thio-beta-d-galactoside).

The grown strain exhibiting white spot on the medium was selected, and cultured in a liquid medium by a conventional method, a plasmid DNA was extracted from the culture solution, and cut with a restriction enzyme to confirm an inserted fragment. As a result, in addition to a plasmid pHSG398 DNA fragment of about 2.2 kb, an inserted DNA fragment of a length of about 3.8 kb containing a PC gene was recognized.

A plasmid containing the PC gene was named as pCRB1-PC. Then, the plasmid pCRB1-PC was introduced into *Corynebacterium glutamicum* R ldh⁻ strain according to an electric pulse method (Y. Kurusu, et al., Agric. Biol. Chem. 54: 443-447. 1990. and A. A. Vertes, et al., Res. Microbiol. 144: 181-185. 1993).

Name of recombinant bacterium; *Corynebacterium glutamicum* R ldh⁻/pCRB1-PC, Independent Administrative Agency Industrial Technical Comprehensive Laboratory, Patent Organism Depository Center, accession number; FERM BP-10060

Regarding PC activity of *Corynebacterium glutamicum* R ldh⁻/pCRB1-PC, about 6-fold increase in the activity was observed as compared with a wild type (*Corynebacterium glutamicum* R) strain, as measured by a PC activity measuring method (Uy., D., S. Delaunay, J. Engasser, and J. Goergen. 1999. A method for the determination of pyruvate carboxylase activity during the glutamic acid fermentation with *Corynebacterium glutamicum*. J Microbiol Methods 39:91-96) and a Western blotting method (Peters-Wendisch, P. G., V. F. Wendisch, S. Paul, B. J. Eikmanns, and H. Sahm. 1997. Pyruvate carboxylase as an anaplerotic enzyme in *Corynebacterium glutamicum*. Microbiology, 143: 1095-1103).

Example 3

Experiment of Culturing Bacterial Cells of Recombinant Strain and Production of Succinic Acid (1) Culturing of *Corynebacterium glutamicum* R ldh⁻/pCRB1-PC strain under aerobic condition:

(Preparation of culture medium); 500 ml of a medium consisting of urea 2 g, ammonium sulfate 7 g, $KH_2PO_4$ 0.5 g, $K_2HPO_4$ 0.5 g, $MgSO_4.7H_2O$ 0.5 g, $FeSO_4.7H_2O$ 6 mg, $MnSO_4.7H_2O$ 4.2 mg, Biotin (biotin) 200 µg, thiamine hydrochloride 200 µg, yeast extract 2 g, casamino acid 7 g, and distilled water 1000 ml was dispensed into a flask having a volume of 1 L, this was heat-sterilized at 120° C. for 10 minutes, and the flask cooled to room temperature was used as a seed culture medium flask. Similarly, 1000 ml of a medium having the same composition was placed into a glass jar fermenter having a volume of 2 L, and this was heat-sterilized at 120° C. for 10 minutes, and used as a principal culture medium jar.

(Culturing): *Corynebacterium glutamicum* R ldh⁻/pCRB1-PC was inoculated on one of the above seed culture medium under the sterile condition, aerobic shaking culturing was performed at 33° C. for 12 hours, and this was used as a seed culture solution. 50 ml of this seed culture solution was inoculated on the jar fermenter, and principal culturing was performed at a temperature of 33° C. overnight at a ventilation amount of 1 vvm (Volume/Volume/Minute). The culture solution was allowed to stand for about 3 hours under the nitrogen gas atmosphere, and 200 ml of the culture solution was subjected to a centrifuge (5000 rotation, 15 minutes) to remove the supernatant. The thus obtained wet bacterial cells were used in the following reaction.

(2) Preparation of Reaction Medium Solution for Reaction:

A reaction stock solution consisting of ammonium sulfate 7 g, $KH_2PO_4$ 0.5 g, $K_2HPO_4$ 0.5 g, $MgSO_4.7H_2O$ 0.5 g, $FeSO_4.7H_2O$ 6 mg, $MnSO_4.7H_2O$ 4.2 mg, Biotin 200 µg, thiamine hydrochloride 200 µg and distilled water 1000 ml was prepared, and the solution was heated at 120° C. for 10 minutes, and dissolved oxygen was removed for 20 minutes under the reduced pressure condition (not more than 3 mmHg). The reducing state of the reaction stock solution was confirmed by the change of color tone (change from blue to colorless) of a reducing state indicator resazurin which had been added to the reaction stock solution at the initiation of reduced pressure. 500 ml of this reaction stock solution was introduced into a glass reaction container having a volume of 1 L under the nitrogen atmosphere. This reaction container is provided with a pH adjusting equipment, a temperature maintaining equipment, an equipment for stirring a reaction solution in a container, and an oxidation-reduction potential measuring equipment.

(3) Implementation of Reaction:

The coryneform bacterium cells prepared after culturing were added to 500 ml of the reaction stock solution in a reaction container under the nitrogen gas atmosphere. Glucose 200 mM and sodium carbonate 200 mM were added, and the reaction temperature was maintained at 33° C. to perform a reaction producing an organic compound. An oxidation-reduction potential was initially −200 mV, but was reduced immediately after the initiation of the reaction, and the reaction was continued by maintaining the oxidation-reduction potential at −400 mV. After the reaction for 3 hours, the reaction medium solution was analyzed by liquid chromatography, indicating that succinic acid 163 mM (19.2 g/L) and malic acid 5 mM (0.67 g/L) were produced. Lactic acid was not detected.

Comparative Example 1

Effect of Disruption of ldh Gene, 1

According to a similar manner and conditions to Example 3 except that the coryneform bacterium used in Example 3 was changed to *Corynebacterium glutamicum* R strain (wild strain) and *Corynebacterium glutamicum* R/pCRB1-PC (strain obtained by transforming a wild strain (*Corynebacterium glutamicum* R strain) with a plasmid pCRB1-PC), organic compounds producing reaction were performed. The transformation was performed according to a similar manner to Example 2(B). After the reaction for 3 hours, the reaction medium solutions were analyzed by liquid chromatography, indicating that *Corynebacterium glutamicum* R strain (wild strain) produced succinic acid 81 mM (9.6 g/L) and lactic acid 200 mM (18.0 g/L), and *Corynebacterium glutamicum* R/pCRB1-PC produced succinic acid 82 mM (9.7 g/L) and lactic acid 202 mM (18.1 g/L). When any strain in comparative example was used, malic acid was not detected.

That is, these experimental results show that ldh disruption in this invention is very effective for improving succinic acid productivity because, even when a PC gene is highly expressed in a wild strain (*Corynebacterium glutamicum* R strain), increase in a production amount of succinic acid is not recognized, and any of them is of succinic acid productivity which is about ½ as compared with *Corynebacterium glutamicum* R ldh⁻/pCRB1-PC strain in Example 3.

Comparative Example 2

Effect of Disruption of ldh Gene, 2

According to a similar manner and condition to Example 3 except that a bacterium strain to be used was changed to *Corynebacterium glutamicum* R ldh⁻ strain prepared by the method described in Example 1(C), an organic compound producing reaction was performed.

After the reaction for 3 hours, the reaction medium solution was analyzed by liquid chromatography, indicating that succinic acid 80 mM (9.4 g/L) was produced. Lactic acid and malic acid were not detected. From this result, it is elucidated that only disruption of an ldh gene does not produce the effect of improvement in succinic acid productivity, and this improved productivity of succinic acid is about 2-fold, which is the effect of the present invention, and is obtained only when associated with highly expressing a PC gene in *Corynebacterium glutamicum* R ldh⁻ strain.

Comparative Example 3

Effect of High Expression of PEPC Gene in ldh Gene-Disrupted Strain

According to a similar manner and condition to Example 3 except that the coryneform bacterium used in Example 3 was changed to *Corynebacterium glutamicum* R ldh⁻/pCRB1-PEPC strain, an organic compound producing reaction was performed.

Generation of a plasmid pCRB1-PEPC was carried out according to the method of Example 2 except that primers for specifically amplifying a PEPC gene which is known in the literature (Appl. Environ. Microbiol., 57: 1746-1752 (1991), Mol. Gen. Genet., 218: 330-339 (1989) and Gene, 77: 237-251 (1989)) was utilized.

That is, amplification was performed by PCR using two kinds of primers;

```
PEPC-N;  5'-CTCTGTCGACAGCACAGCCTTAA (SEQ ID NO: 9)
         AGCA-3'

PEPC-C;  5'-CTCTGTCGACTTGTGCAGCAAGA (SEQ ID NO: 10)
         CGAAA-3'
```

(In both primers, a SalI site is added to the terminus as shown in the underlined part) and, as a template DNA, a chromosome DNA of *Corynebacterium glutamicum* R strain, and a plasmid pCRB1-PEPC was generated by a method of introducing into a SalI site of a coryneform bacterium-*Escherichia coli* shuttle vector pCRB1.

In addition, transformation into *Corynebacterium glutamicum* R ldh⁻ strain was according to the method of Example 2. When PEPC activity was compared by the method of the literature (J. Bacteriol., 179:4942-4945 (1997)), PEPC activity of *Corynebacterium glutamicum* R ldh⁻/pCRB1-PEPC strain was increased 4-fold as compared with *Corynebacterium glutamicum* R ldh⁻ strain.

After the reaction for 3 hours, the reaction medium solution was analyzed by liquid chromatography, and indicated that succinic acid 83 mM (9.8 g/L) was produced. Lactic acid was not detected. It is elucidated that even when a PEPC gene is highly expressed in *Corynebacterium glutamicum* R ldh⁻ strain, productivity of succinic acid is not improved.

Example 4

Effect of Additional Introduction of FRD Gene

According to a similar manner and condition to Example 3 except that the coryneform bacterium used in Example 3 was changed to *Corynebacterium glutamicum* R ldh⁻/pCRB1-PC-FRD strain, an organic compound producing reaction was performed.

A plasmid pCRB1-PC-FRD is such that a fumarate reductase gene (enzyme name is abbreviated as FRD, and gene name is abbreviated as frd) derived from *Escherichia coli* is ligated to the plasmid pCRB1-PC constructed in Example 2(B). Fumarate reductase is an enzyme which catalyzes conversion of fumaric acid into succinic acid in the tricarboxylic acid cycle.

Generation of the plasmid pCRB1-PC-FRD was performed by the following method.

Cloning of a frd gene derived from *Escherichia coli* was performed according amplification by PCR and, upon PCR, in order to clone a frd gene, based on the results of entire genome analysis of *Escherichia coli* (K-12 strain (see The complete genome sequence of *Escherichia coli* K-12 Science, 277(5331), 1453-1474 (1997)), the following one pair of primer were synthesized using "394 DNA/RNA synthesizer" manufactured by Applied Biosystems, and were used.

Primers for amplifying frd gene

```
frd-N; 5'-CTCTGCATGCGGATGCCGTTTCGC (SEQ ID NO: 11)
       TCATAG-3' frd-C; 5'-CTCTGCATGCTAATAAGGCGCAGA (SEQ ID NO: 12)
       GCGTCG-3'
```

In any primer, a SphI site is added to the terminus.

According to a similar to Example 1(A), a total DNA was prepared from *Escherichia coli* K-12 MG1665 strain, and this was used as a template DNA.

PCR was performed under similar conditions to Example 1(B).

10 µl of the reaction solution produced above was electrophoresed on a 0.8% agarose gel and, in the case of a frd gene, a DNA fragment of about 3.8 kb could be detected.

Then, 10 µl of the 3.8 kb PCR product containing a frd gene which had been cut with a restriction enzyme SphI and 2 µl of the plasmid pCRB1-PC constructed in Example 2(B) which had been cut with a restriction enzyme SphI was treated at 80° C. for 10 minutes, respectively, to inactivate restriction enzymes, and both were mixed. Respective components of 1 µl of T4 DNA ligase 10× buffer and 1 unit of T4 DNA ligase were added thereto, and sterile distilled water was added to an amount of 10 µl, followed by the reaction at 15° C. for 3 hours. Using this ligation solution, *Escherichia coli* JM109 (manufactured by TAKARA SHUZO CO., Ltd.) was transformed by a calcium chloride method (Journal of Molecular Biology, 53, 159 (1970)), and this was smeared on a medium (10 g of tryptone, 5 g of yeast extract, 15 g of NaCl and 16 g of agar were dissolved in 1 L of distilled water) containing 50 mg of chloramphenicol.

A strain growing on the medium was cultured in a liquid medium by a conventional method, and a plasmid DNA was extracted from the culture solution and cut with a restriction enzyme, thereby to confirm an inserted fragment. As a result, in addition to a plasmid pCRB1-PC DNA fragment of about 6.0 kb, an inserted DNA fragment of a length of about 3.8 kb containing a frd gene was recognized.

The plasmid containing the PC gene was named as pCRB1-PC-FRD.

Then, the plasmid pCRB1-PC-FRD was introduced into *Corynebacterium glutamicum* R ldh⁻ strain according to an electric pulse method (Y. Kurusu, et al., Agric. Biol. Chem. 54: 443-447, 1990. And A. A. Vertes, et al., Res. Microbiol. 144: 181-185, 1993).

This strain was designated as *Corynebacterium glutamicum* R ldh⁻/pCRB1-PC-FRD strain (this recombinant bacterial strain has been deposited at Independent Administrative Industrial Technical Comprehensive Laboratory, Patent Organism Depository Center at an accession number: FERM BP-10061 under a bacterial name; *Corynebacterium glutamicum* R ldh⁻/pCRB1-PC-FRD).

Enzyme activity of a pathway from fumaric acid to succinic acid in the present bacterial strain was measured by the method described in (ELENA MAKLASHINA, et al., J. Bacteriology, 180: 5989-5996, 1998), and it was found that enzyme activity of the present pathway was increased 3-fold as compared with a parent strain before transformation.

Reaction was performed for 3 hours using the present *Corynebacterium glutamicum* R ldh⁻/pCRB1-PC-FRD strain, and the reaction medium solution was analyzed by liquid chromatography, and it was found that succinic acid 168 mM (19.8 g/L) was produced. Lactic acid and malic acid were not detected.

From this, when *Corynebacterium glutamicum* R ldh⁻/pCRB1-PC strain and *Corynebacterium glutamicum* R ldh⁻/pCRB1-PC-FRD strain are compared, by allowing a strain which has highly expressed a PC gene in an ldh gene-disrupted strain to further highly express a frd gene derived from *Escherichia coli*, an amount of produced succinic acid is increased and, at the same time, dicarboxylic acid having a high purity can be recovered, and it is clear that this is a useful technique from a viewpoint of separation and purification of dicarboxylic acids.

INDUSTRIAL APPLICABILITY

Dicarboxylic acids produced by the present invention are used in a wide application such as polymer synthesis raw material, medicament raw material and cosmetic utility, and food additive utility. For example, succinic acid and derivatives thereof are used in utility of a biodegradable plastic raw material and a green cleaning solvent with in no environmental pollution.

The invention claimed is:

1. A process for producing dicarboxylic acids selected from the group consisting of succinic acid, fumaric acid and malic acid, which comprises reacting a bacterium and saccharides in a reaction solution under the reducing state containing carbonate or bicarbonate ions or carbon dioxide gas therein, and collecting dicarboxylic acids produced in the reaction solution, wherein the bacterium is an aerobic *Corynebacterium glutamicum* R transformant wherein
   a) the endogenous lactate dehydrogenase gene is disrupted by a homologous recombination method with a plasmid and said *Corynebacterium* bacterium is transformed with
   b) the pyruvate carboxylase gene derived from *Corynebacterium glutamicum* R strain wherein said gene is overexpressed and wherein an oxidation-reduction potential of the reaction solution under the reducing state is −200 millivolts to −500 millivolts.

2. The process for producing dicarboxylic acids according to claim 1, wherein the aerobic *Corynebacterium glutamicum* R transformant is *Corynebacterium glutamicum* R ldh⁻/pCRB1-PC (FERM BP-10060) or *Corynebacterium glutamicum* R ldh⁻/pCRB1-PC-FRD (FERM BP-10061).

* * * * *